US005710174A

United States Patent [19]
West et al.

[11] Patent Number: 5,710,174
[45] Date of Patent: Jan. 20, 1998

[54] FACTOR XIIIA INHIBITOR

[75] Inventors: Robert R. West, Seattle; Teresa Martinez, Oak Harbor; Hank R. Franklin, Seattle; Paul D. Bishop, Fall City, all of Wash.; Birgitte Rømer Rassing, Copenhagen, Denmark

[73] Assignees: Zymo Genetics, Inc., Seattle, Wash.; Novo Nordisk A/S, Bagsvaerd, Denmark

[21] Appl. No.: 483,213

[22] Filed: Jun. 7, 1995

[51] Int. Cl.$^6$ .................................................. A61K 31/335
[52] U.S. Cl. .................................. 514/450; 549/270
[58] Field of Search .......................... 514/450; 549/270

[56] References Cited

U.S. PATENT DOCUMENTS 5,030,644  7/1991  Baldwin et al. ........................ 514/393
5,188,830  2/1993  Atkinson et al. ..................... 424/94.63

OTHER PUBLICATIONS

Edwards et al., *Fibrinolysis* 7: 21–216, 1993.
Colman et al. (eds.), *Hemostasis and Thrombosis, Basic Principles and Clinical Practice*: 269–288, 1987.
Shebuski et al., *Blood* 75(7): 1455–1459, 1990.
Freund et al., *Biochemistry* 33: 10109–10119, 1994.
Cutler et al., *Proceedings of the 14th Annual Plant Growth Regulator Society of America*: 236–247, 1987.
Lai et al., *Bull. Chem. Soc. Japan* 64(3): 1048–1050, 1991.
Leidy et al., *Thrombosis Research* 59:15–26, 1990.
Sassa et al., *Nippon Kagaku Kaishi* 5:883–885, 1981.
Oyama et al., *Agric. Biol. Chem.* 42(12): 2407–2409, 1978.
Nukina, M. et al. "Structures and Biological Activities of Fungal Macrolides, Pyrenolide and Resorcylide" CA93:127097 (1980).
Sassa, T. et al. "Electrophilic Reactivities and Biological Activities of Trans– and Cis Resorcylides" CA95:115254 (1981).
Oyama, H. et al. "Structures of New Plant Growth Inhibitors, Trans– and Cis Resorcylide" CA90:116741 (1979).

*Primary Examiner*—Amelia Owens
*Attorney, Agent, or Firm*—Janet Sleath; Ann W. Speckman

[57] ABSTRACT

A compound that is useful for inhibiting FXIIIa catalysis of fibrin cross-linking, and related pharmaceutical compositions and methods, are disclosed. The compound and compositions may be advantageously used to enhance fibrinolysis and resolution of blood clots.

9 Claims, No Drawings

FACTOR XIIIA INHIBITOR

TECHNICAL FIELD

The present invention relates to compositions and methods for preventing hard clot formation. More specifically, the invention relates to a Factor XIIIa inhibitor and prophylactic or therapeutic methods useful after initial relief from a thrombotic attack is achieved.

BACKGROUND OF THE INVENTION

Thrombosis is the formation, development or existence of a blood clot within the vascular system. This is a life-saving process when it occurs during hemorrhage. It may be a life-threatening event when it occurs at any other time, because the clot can occlude a vessel and impair or prevent blood supply to an organ or other vital part of the body. The blood clot, if detached, becomes an embolus, and may occlude a vessel at a distance from the original clot site; for example, a clot in the leg may break away from the original clot site and cause a pulmonary embolus.

Removal of an occluding blood clot by lysis is essential, and the rate of lysis may be critical in ultimate patient recovery. Clot lysis normally occurs within hours or days through the action of a proteolytic enzyme called plasmin. The precursor to plasmin, plasminogen, is present in plasma and is activated by enzymes including prourokinase (single chain urokinase), urokinase (dual chain urokinase), streptokinase, eminase (European Patent Application No. 028,489), or tissue plasminogen activator ("t-PA"). However, since the occurrence of a blood clot can call for rapid remedial action, administration of plasminogen or a plasminogen activator does not always achieve lysis fast enough to minimize injury to cells, tissues, or organs.

Activated factor XIII ("FXIIIa") is an enzyme that catalyzes a number of covalent cross-linking reactions of fibrin in blood clots. These covalent fibrin cross-linking reactions render blood clots mechanically stable and greatly increase clot resistance to plasma degradation (fibrinolysis). Specifically, FXIIIa catalyzes linear cross-linking between the gamma ("$\gamma$") chains of fibrin to form $\gamma$ dimers. This reaction is very quick (in plasma it occurs within 30 minutes or less) and gives mechanical strength to the clot.

Simultaneous with catalyzing $\gamma$ chain cross-linking, FXIIIa catalyzes cross-linking of fibrin alpha ("$\alpha$") chains to a plasminogen inhibitor, $\alpha_2$-PI. This $\alpha_2$-PI incorporation into a cross-linked clot gives a clot immediate protection against fibrinolysis. Subsequently, and at much slower rates (up to 6 days) in a clot, FXIIIa catalyzes lateral cross-linking of $\alpha$ chains to form clusters of five to seven $\gamma$ chains. In addition, FXIIIa catalyzes (i) $\alpha$ chain cross-linking to $\gamma$ dimers; and (ii) $\gamma$ dimer cross-linking with other $\gamma$ chains to form $\gamma$ trimers and tetramers. In general, the older the clot, the greater amount of the fibrin cross-linking and the greater resistance to clot lysis.

After a clot that has caused a myocardial infarction has been lysed, the reformation of a second or third clot at the same site becomes more life-threatening than the formation of the first clot. This is because, when the first occluding clot is lysed, it is common that not all of the clot is dissolved. As blood flow is restored over the undissolved portion of the clot, some blood constituents cause platelet deposition and promote further thrombosis. When this happens, the natural hemostatic balance (the balance between clot formation and clot degradation) is shifted from fibrinolysis toward thrombosis. The surface of any undissolved portion of the first clot is intrinsically thrombogenic, and more fibrin is often deposited before resolution of the first clot is complete. This newly deposited fibrin gives the older, undissolved portion of the clot an enhanced opportunity to become more cross-linked. As a clot persists over time, more fibrin cross-linking occurs, and the denser and more resistant to fibrinolysis the clot becomes, until a hard clot is formed, i.e., a very mature, fibrin-dense clot.

To prevent formation of fibrinolysis-resistant clots, a commonly administered oral anticoagulant is dicoumarin. Dicoumarin inhibits the proper formation of clotting proteins via mechanisms in the liver involving gamma carboxylation of the clotting proteins. In general, dicoumarin impairs the body's ability to make coagulation factors. However, the beneficial effects of dicoumarin are not immediately achieved—generally a three to eight day period of administration is needed for effective clot inhibition. Additionally, administration of dicoumarin is associated with toxicity. Dicoumarin affects homeostatic balance, such that thrombosis is reduced, i.e., clot formation is diminished or inhibited. Consequently, the patient is more prone to internal bleeding.

In contrast, FXIIIa inhibitors do not prevent clot formation; instead, FXIIIa inhibitors aid in clot resolution if one or more clots form. This mode of action is consistent with evidence that Factor XIII-deficient patients have "weak" clots that are easy to lyse. Since FXIII inhibitors do not affect homeostatic balance, a FXIII inhibitor does not have the undesirable side-effect of overt bleeding or toxicity.

Accordingly, there is a need for compounds, compositions and methods that reduce or eliminate FXIIIa cross-linking of fibrin in clots that occurs when the hemostatic balance shifts toward thrombosis.

SUMMARY OF THE INVENTION

The present invention provides a novel FXIIIa inhibitor, ZG-1400 (defined below), that (i) inhibits FXIIIa catalysis of covalent cross-linking reactions of fibrin; and (ii) enables plasmin to more rapidly lyse blood clots. The present invention also provides methods for preventing hard clot formation that comprise administering a therapeutically effective amount of ZG-1400, alone or in combination with plasminogen; one or more plasminogen activators; or a combination of plasminogen and one or more plasminogen activators. Exemplary plasminogen activators may be isolated from natural sources or produced by recombinant technology, and include genetically engineered variants thereof. The methods disclosed herein are useful for maintaining vessel patency after initial relief from thrombotic attack has been achieved. These methods feature inhibition of FXIIIa catalysis of cross-linking reactions in a clot, thereby minimizing complications that may result from occlusion or reocclusion. The claimed methods may be useful prophylactically if one administers ZG-1400 to a patient considered to be at high risk for thrombosis.

These and other aspects of the present invention will become evident upon reference to the following detailed description.

DETAILED DESCRIPTION OF THE INVENTION

As noted above, the present invention provides a compound, designated herein as ZG-1400, that inhibits the action of FXIIIa, a transglutaminase enzyme. As used herein, the term "inhibitor" includes, but is not limited to, a compound that provides complete or partial inhibition of a given activity, down-regulation of that activity, or antagonism of the target activity. In general, ZG-1400 renders blood clots more susceptible to lysis by plasminogen or other thrombolytic agents.

ZG-1400 can be isolated and purified by aerobic fermentation of fungal culture M00811, originally isolated from a soil sample collected in Mexico. The culture was taxonomically characterized as *Penicillium roseopurpureum* at Centraalbureau voor Schimmelcultures, Oosterstraat 1, 3742 SK Baarn, The Netherlands.

This fungus is maintained in the Culture and Metabolites Collection of Novo Nordisk A/S, Novo Alle, 2880 Bagsvaerd, Denmark as culture number NN006817/ CL1140-3. A viable culture of this microorganism was deposited with the Centraalbureau voor Schimmelcultures, Oosterstraat 1, 3742 SK Baarn. The Netherlands on Feb. 20, 1995. It has been deposited under the Budapest Treaty and assigned the strain designation CBS 170.95 by such depository.

ZG-1400 was discovered through the use of a high throughput screening process. This process involved preparation of 11,198 different microbial cultures, extracting the cultures with ethyl acetate, and screening the extracts for FXIIIa inhibition.

A non-homogeneous crude test sample was prepared by growing *P. roseopurpureum* in an appropriate culture medium. For fermentation, 3 ml of a spore/mycelium suspension of CBS 170.95 was used to inoculate 250 ml baffled shake flasks containing 100 ml of YES medium each (sucrose, 150 gm/l; yeast extract (BACTO, Difco Laboratories, Detroit, Mich.), 20 g/l; $ZnSO_4 \cdot 7\ H_2O$, 0.0178 g/l; $CUSO_4 \cdot 5\ H_2O$, 0.0078 g/l, combined in deionized water and adjusted to about pH 6.4). The flasks were incubated for 12 d at 26° C. at 200 RPM of rotation.

A one liter fermentation batch of *P. roseopurpureum* was prepared by inoculating 1 ml of frozen 30% glycerol stock culture into 10.0 ml sterile water. Then 1.0 ml of that solution was added to each of ten 500 ml baffled flasks containing 100 ml of culture medium. Each 500 ml flask has four bottom baffles (e.g., Kimax No. 26505 flasks, Wheaton, Millville, N.J.). The inoculated medium was then cultured for 14 d at 150 RPM and 26° C.

After 12–14 d incubation, the entire culture (medium plus cells) was combined with ethyl acetate in a 1:1 ratio and vigorously agitated overnight at 20° to 25° C. The ethyl acetate-culture mixture was then centrifuged at 300 RPM for 20 min. The supernatant was decanted and the organic layer evaporated to dryness. The dried crude organic extract then was resuspended in a fixed amount of DMSO relative to the original culture volume. This extract was screened for FXIIIa inhibition at a variety of final extract concentrations in the primary FXIIIa screening assay described below.

The primary FXIIIa screening assay used a 96-well high throughput assay format. This assay assesses test sample inhibition of FXIIIa catalyzed cross-linking of biotinylated fibrinogen and immobilized fibronectin. Collagen, actin, myosin, dansylcadaverine, putrescine, and casein can also be cross-linked by FXIIIa and, therefore, may be substituted for fibrinogen or fibronectin in this assay.

Fibrinogen is a precursor to fibrin. Fibronectin is not related to fibrin, but it is a normal constituent of a plasma clot. Fibronectin is cross-linked into and attached to a plasma clot by FXIIIa, and can account for as much as 10% of the clot weight. Fibronectin is a preferred substrate for the primary screening assay because it adheres to 96 well plates more readily than fibrinogen.

Test samples (possibly containing FXIIIa inhibitors) were added to 96-well plates coated with fibronectin, followed by the addition of FXIIIa, as described in the primary FXIIIa screening assay, below. Biotinylated fibrinogen was added to the wells, and streptavidin-alkaline phosphatase was used to detect biotinylated fibrinogen that had been cross-linked to fibronectin. One of ordinary skill in the art will recognize that other detectable signal systems (such as radiolabeled, fluorescent-labeled or other colorimetric signal systems) can be used in place of the streptavidin-biotin colorimetric system exemplified herein. If a test sample did not inhibit FXIIIa, cross-linking was detected. If a test sample inhibited FXIIIa, no cross-linking or significantly reduced levels of cross-linking were observed as compared to controls that did not receive a test sample.

PRIMARY FXIIIa SCREENING ASSAY

Fibronectin (Enzyme Research Labs, Inc., South Bend, Ind.) was purified according to F. Grinell et al., Cell, 19:517–25, 1980. Purified fibronectin was diluted to 1 µg/ml in 0.1M $Na_2CO_3$, pH 9.7, and added to control and test assay wells of 96-well plates at 100 µl/well. All wells were incubated overnight at 4° C.

After incubation, the plate wells were washed twice with 200 µl/well of wash buffer per wash to remove all fibronectin not bound to the wells. The wash buffer contained 0.135M NaCl, 2.7 mM KCl, 25 mM Tris at about pH 7.4, and 0.1% Tween 20® (Sigma Chemical Co., St. Louis, Mo.; polyoxyethylenesorbitan monolaurate). The plate wells were then blocked with 200 µl/well blocking buffer and incubated for 1–2 h at 37° C. The blocking buffer contained 0.135M NaCl, 2.7 mM KCl, 25 mM Tris at about pH 7.4, 0.1% Tween 20®, and 0.5% BSA (bovine serum albumin, Sigma fraction V; Sigma). After incubation, the plates wells were again washed with 200 µl/well of wash buffer to remove excess blocking buffer.

Biotin was conjugated to fibrinogen (using D-biotin-N-hydroxysuccinimide ester (BNHS, Boehringer Mannheim, Indianapolis, Ind.)) according to the method of K. Hoffman et. al., *J. Am. Chem. Soc.* 100:3585, 1978. Briefly, fibrinogen was dialyzed against 0.1M $NaHCO_3$, pH 8.5 (coupling buffer) at a concentration of 1 mg/ml. BNHS was dissolved in dimethylformamide at a concentration of 1.7 mg/ml, and added to fibrinogen in coupling buffer at a ratio of 30 µl BNHS to 1 ml fibrinogen. The mixture was incubated with rocking for 4 h at room temperature, dialyzed against PBS, and stored in aliquots at –80° C.

Biotinylated fibrinogen (40 µl of 20 µg/ml solution) was added to each plate well. Except in control wells (which received 10 µl of 10% DMSO alone), 10 µl of each of the 11,198 crude extracts in 10% DMSO were added to duplicate wells after the addition of biotinylated fibrinogen, resulting in a 1% final assay concentration of DMSO.

FXIIIa (recombinant human $FXIIIa_2$ (ZymoGenetics), as described in European Patent No. 0 268 772, granted Apr. 26, 1995, and incorporated herein by reference) was diluted to 100 µg/ml in a solution of 50 mM Tris, 5 mM $CaCl_2$ at pH 7.4 containing 1 unit/ml thrombin (bovine; Enzyme Research Labs) and incubated for 20 min at 37° C. FXIIIa then was diluted to 1 µg/ml in a cross-linking buffer consisting of the blocking buffer described above plus 20 mM $CaCl_2$ and 75 ng/ml D-phenylalanyl-L-prolyl-L-arginine chloromethyl ketone (PPACK; Calbiochem, La Jolla, Calif.). Fifty microliters of FXIIIa in cross-linking buffer was added to each test and control well. All wells then were incubated for about 10 min at 37° C.

After incubation, the wells were washed twice with 200 µl/well of wash buffer to remove all biotinylated fibrinogen that was not cross-linked to fibronectin. Then 100 μl streptavidin-alkaline phosphatase (Amersham, Arlington Heights, Ill.) diluted to 1:2000 in wash buffer plus 0.5% crystalline BSA (American Research Products, Solon, Ohio) was added to each control and test well. All wells were incubated for about 45 min at 37° C.

The plate wells were washed three times with 200 μl/well of wash buffer to remove streptavidin-alkaline phosphatase not bound to cross-linked biotinylated fibrinogen. Substrate was prepared by adding 6 mg phosphatase substrate (Sigma) per ml of 96 ml diethanolamine (Sigma), 56 mg $MgCl_2$, and $H_2O$ to one liter at about pH 9.8. About 100 μl of phosphatase substrate was added to each plate well. If streptavidin-alkaline phosphatase was bound to biotinylated fibrinogen, the substrate was cleaved, producing a colorimetrically detectable product. Absorbance was read at 405 nm on a ThermoMax microplate reader (Molecular Devices, Menlo Park, Calif.). Inhibition was measured as a percent reduction of cross-linking by a test sample as compared to control wells containing only FXIIIa and test sample diluent.

The advantage of this primary FXIIIa screening assay over fluorometric or other signal assays is that unbound reagents and test samples are washed from the wells before signal development and detection, thereby reducing interference due to crude extract biomass. The crude extracts that reduced cross-linking in the primary FXIIIa screening assay by greater than three standard deviations from the control cross-linking value were considered potential FXIIIa inhibitors. These potential FXIIIa inhibitors were retested in the primary FXIIIa screening assay using 100- to 1000-fold serial dilutions of test sample. The crude extract from *Penicillium roseopurpureum* culture CBS 170.95 yielded ZG-1400, and produced about 51% inhibition of FXIIIa-catalyzed cross-linking in the primary FXIIIa screening assay at a 0.1X culture concentration.

tTG SCREENING ASSAY

Because FXIII is a member of the tissue transglutaminase (tTG) family, all potential FXIIIa inhibitors identified in the primary FXIIIa screening assay were further screened for tTG (non-FXIII-specific) inhibitory activity. The tTG screening assay was identical to the primary FXIIIa screening assay, except that tTG (Sigma) was used instead of FXIIIa and no thrombin or PPACK was used.

ZG-1400 inhibited tTG about 70% at a 0.1X concentration. In addition, ZG-1400 was tested at a 0.01X concentration, and showed about 65% inhibition of FXIIIa and about 95% inhibition of tTG. The increase in FXIIIa and/or tTG inhibitory activity at lower dilutions was observed with other crude extracts, and may be attributed to biomass within the crude extracts masking inhibition at higher concentrations. However, rescreening of selected extracts at lower dilutions in the primary and tTG screening assays did not yield any additional potential FXIIIa-specific inhibitors.

PURIFICATION AND CHARACTERIZATION OF ZG-1400

Two protocols have been developed to purify ZG-1400. The original protocol was developed on the basis of the impure material's biological activity. A simplified protocol was later developed based on ZG-1400's chemical properties. For both purification protocols, *P. roseopurpureum* CBS 170.95 was cultured as described above for the screening assays.

Original ZG-1400 purification protocol

A one liter fermentation batch of *P. roseopurpureum* CBS 170.95 was prepared as described previously. After incubation, 100 ml aliquots of each *P. roseopurpureum* preparation were transferred to a 250 ml kautex bottle and homogenized with a homogenizer. This homogenate was combined with ethyl acetate (1:1) and vigorously stirred for 16 to 18 h at room temperature. The ethyl acetate/homogenate mixture was centrifuged for 10 min at 1500×g. The ethyl acetate phase was removed. If turbid, the ethyl acetate phase was filtered through a 0.45 μm filter. The ethyl acetate phase was evaporated to dryness.

The total dried organic material then was dissolved into 270 ml methanol. Approximately 30 ml water was then added to the dissolved organic material. This mixture was partitioned with 100 ml of hexane and the layers were allowed to separate. The procedure was repeated two more times. Then 147 ml of water was added to the methanol/water layer, and this layer was partitioned three times with chloroform. The chloroform layers were combined and evaporated to dryness.

The dry, chloroform-soluble material was dissolved in 20 ml methanol and filtered through a 0.45 μm filter. Filtered material (40 to 50 mg in 1 ml of methanol) was applied to a preparative high performance liquid chromatography reverse phase C18 (reverse phase HPLC) column (e.g., Vydac™ (Hewlett Packard, Wilmington, Del.) C18 matrix, 22.4×250 mm, 300 Å) using a 20 ml/min flow rate and a gradient elution of 10% to 75% acetonitrile in water over 60 min. Biologically active fractions eluted between 29 and 32 min. Fractions were collected every minute (20 ml/fraction), and 1 ml of each fraction was evaporated. The dried fraction sample was redissolved in DMSO and analyzed for biological activity in the primary FXIIIa or tTG screens. Based on these bioassay results, the active fractions were combined, evaporated to dryness and weighed. The dried material was then redissolved into about 2 ml methanol and passed through a small column of celite:carbon (1:5) in order to remove color.

Decolorized material was applied to a second preparative reverse phase HPLC C18 column. Eluted fractions were assayed for biological activity using the primary FXIIIa screening assay. Active fractions were combined to yield 5–8 mg of purified ZG-1400 (designated ZG-1400a).

Simplified ZG-1400 purification protocol

The dried organic material was dissolved into methanol, partitioned with hexane, and partitioned with chloroform, as described in "Original ZG-1400 purification protocol." The chloroform layers were combined and evaporated to dryness. The dry, chloroform-soluble material was dissolved in about 100 ml ethyl acetate. Approximately 25 g silica gel (Bakerbond, 40M, VWR, Seattle, Wash.) was added to the ethyl acetate-dissolved material, and this preparation was evaporated to dryness in a large round bottom flask (so that the extract material was absorbed onto the silica gel). The silica gel-absorbed extract material was applied to the top of a silica gel column (Bakerbond, 40M, 6"×1.5") that was packed with hexane: ethyl acetate (1:1). The column was eluted with hexane: ethyl acetate (1:1) under nitrogen pressure. Eluate fractions showing activity in the primary FXIIIa screening assay described above were combined and evaporated to dryness.

Final purification was achieved by dissolving the dried eluate in 2 ml methanol and injecting this methanol/eluate material onto a preparative C18 reverse phase HPLC column. Fractions were eluted using a 20 ml/min flow rate and a gradient elution of 10% to 75% acetonitrile in water over 60 min. Relevant fractions were detected using 220 nm UV absorbance. Biologically active compound eluted at around 28–30 min using this system. Eluted fractions were collected at 1 min intervals.

These fractions were applied to an analytical C18 reverse phase HPLC column with a flow rate of 1 ml/min and a gradient elution of 15 to 100% acetonitrile in water over 40 min. Relevant fractions were detected using UV absorbance at 220 nm and 280 nm. Fractions containing biologically active compound (ZG-1400) were combined and dried using a speed vacuum (Savant Instruments, Inc., Farmingdale, N.Y.).

Characterization of ZG-1400a

ZG-1400a, an R(–) enantiomer of cis-resorcylide, has the following physiochemical characteristics:

High resolution fast atom bombardment mass spectral analysis of ZG-1400a gave an $(M+H)^+$ ion at 291.1221, which corresponds to a molecular formula of $C_{16}H_{19}O_5$ with a calculated $(M+H)^+=291.1232$.

Melting point: 200°–204° (dec).

Optical Rotation: $[\alpha] D^{24}$ –21.82

Proton nuclear magnetic resonance ($^1$H-NMR) in Acetone-d6 ($\delta$) at 500 MHz: 1.300 (3H, d, J=6 Hz), 1.68 (3H, m), 1.88 (1H, m), 2.170 (1H,m), 2.540 (1H, m), 3.707 (1H, d, J=18.5 Hz), 4.595 (1H, d, J=18.5 Hz), 5.03 (1H, m), 5.786 (1H, ddd, J=6, 10, 11.5 Hz), 6.262 (1H, d, J=2.5 Hz), 6.327 (1H, d, J=2.5 Hz), 6.520 (1H, d, J=11.5 Hz), 9.194 (1H, bs), 12.028 (1H, s).

Carbon-13 nuclear magnetic resonance ($^{13}$C-NMR) in Acetone-d6 ($\delta$) at 75 MHz: 21.48 (CH$_3$), 26.05 (CH$_2$), 27.13 (CH2), 31.87 (CH2), 51.18 (CH2), 76.48 (CH), 102.66 (CH), 106.30 (Q), 113.61 (CH), 132.92 (CH), 138.52 (CH), 140.61 (Q), 163.25 (Q), 166.88 (Q), 172.57 (Q), 201.51 (Q).

Ultraviolet absorption spectrum: $\lambda$ max (EtOH):215 (log $\epsilon$, 4.19), 226 sh (log $\epsilon$, 4.04), 265 (log $\epsilon$, 3.83), 303 (log $\epsilon$, 3.63).

Infrared absorption spectrum (FT-IR): (KBr):3386 (br), 1678, 1643, 1602, 1442, 1398, 1313, 1267 cm$^{-1}$.

The chemical structure of ZG1400a is shown below.

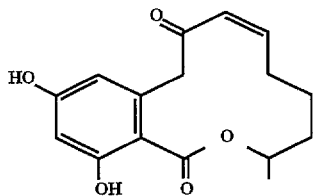

Determination Of IC$_{50}$ Values

IC$_{50}$ refers to the molar concentration of a compound that gives 50% inhibition of FXIIIa. The determination of IC$_{50}$ values was done the same as in the primary FXIIIa screening assay, except that purified compounds were used at varying concentrations (instead of crude culture extracts). The IC$_{50}$ values allow one to make comparisons of one compound to another. Table 1 shows the comparative IC$_{50}$ values for FXIIIa and tTG inhibition by ZG-1400a, iodoacetamide (Sigma), iodoacetic acid (Sigma) and cerulenin (2,3-epoxy-4-oxo-7,10-dodecadienamide, Sigma).

TABLE 1

Inhibition concentration (IC$_{50}$) values FXIIIa and +TG Screens 6

| Compound | FXIIIa Primary Screen | tTG Screen |
|---|---|---|
| ZG-1400 | 5.7 µM | 3.1 µM |
| Iodoacetamide | 320 µM | 10 µM |
| Iodoacetic Acid | 350 µM | 32 µM |
| Cerulenin | 29 µM | 25 µM |

Secondary Screening Procedures

A panel of secondary screening assays was used to confirm FXIIIa inhibitory activity of ZG-1400a. Specifically, these secondary screening assays tested ZG-1400a for inhibition of fibrinogen clotting; inhibition of other blood clotting factors (Factor VIIa ("FVIIa"), Factor IX ("FIX"), Factor Xa ("FXa"), and thrombin); inhibition of papain (which utilizes a cysteine thiol active site that is similar to one present in FXIII and tTG); and plasma clot lysis.

Iodoacetamide and iodoacetic acid are alkylating agents, and were used as comparative (FXIIIa-inhibiting) controls in some of the secondary screening assays. Cerulenin is a transglutaminase inhibitor and also was used as a comparative control. The iodoacetamide or iodoacetic acid were added in a solution containing 10% DMSO to give a final assay concentration of 1% DMSO. Cerulenin is soluble in ethanol, but not DMSO, so cerulenin was similarly prepared in ethanol to give a final assay concentration of 1% ethanol.

Fibrinogen clotting assay

Clots were formed in 1.5 ml Eppendorf tubes by adding reagents to give the following final assay concentrations in a total volume of 100 µl: 2 mg/ml FXIII-free fibrinogen purified on a rabbit anti-FXIII column (Enzyme Research Labs); 20 mM CaCl$_2$; 1 unit/ml thrombin (bovine, Enzyme Research Labs); and either 1 µg/ml FXIIIa (recombinant human FXIIIa$_2$ (ZymoGenetics)) or 20 µg/ml tTG (Sigma) in 120 mM NaCl plus 25 mM Tris at about pH 7.2. In addition, 10 µl of one of the following was added to each tube in varying concentrations to determine a dose response: iodoacetamide, ZG-1400a or cerulenin. The iodoacetamide and ZG-1400a were individually prepared in 10% DMSO and tested at the concentrations shown in Table 2. Cerulenin was prepared in 10% ethanol and tested at the concentrations shown in Table 2. The final reaction volume in each Eppendorf tube was adjusted to 100 µl with 120 mMNaCl plus 25 mM Tris at about pH 7.2.

A positive (complete cross-linking) control contained fibrinogen, enzyme (FXIIIa or tTG), calcium, and thrombin at final assay concentrations listed above, and was tested in the absence of any inhibitor. A negative (no cross-linking) control contained a solution of FXIII-free fibrinogen, thrombin and 20 µM EDTA [(ethylene dinitrilo)tetraacetic acid, disodium salt, dihydrate (J. T. Baker, Phillipsburg, N.J.)] in the absence of calcium and enzyme. Both positive and negative controls contained a final DMSO concentration of 1%. The FXIIIa-treated clots and their controls were incubated for about 10 min at about 37° C., while the tTG-treated clots and their controls were incubated for about 4 h at about 37° C. After incubation, all of the clots and controls were frozen to quench reactions.

Frozen clots and controls were boiled for about 3 min, centrifuged at 14,000 RPM for 5 min, and then the supernatant was removed. The clots were resuspended in 100 μl lysis buffer and incubated overnight at 37° C. The lysis buffer Contained 10M urea, 10 mM EDTA, 1% sodium dodecyl sulfate ("SDS"), and 1% 2-mercaptoethanol. After incubation, approximately 5 μl of each sample was brought to a final volume of 20 μl with a reducing sample buffer (containing 125 mM Tris, pH 6.8, 20% glycerol, 4% SDS, 10% 2-mercaptoethanol, and 0.025% bromophenol blue), and applied to 4–15% gradient gels (Integrated Separation Systems, Natick, Mass.) for polyacrylamide electrophoresis (PAGE) at 200 volts for approximately 1 h or until the tracking dye reached the bottom of the gel.

After staining with Coomassie blue, the alpha, beta, and gamma chains of fibrin were visualized as bands on the gel. The presence of FXIIIa-catalyzed fibrin cross-linking was observed by the appearance of a gamma-gamma dimer, and the disappearance of the monomeric gamma band from the gels. The tTG cross-linking occurs by formation of alpha chain polymers and alpha$_2$-gamma oligomers. Since there are many bands, they are difficult to visualize. A better indication of tTG cross-linking was the disappearance of the monomeric alpha band from the gels. In addition, the gamma band was reduced, but to a lesser degree than in FXIIIa cross-linked clots.

The gels were also scanned on a densitometer (Bio Image Whole Band Analyzer, Millipore Corp., Bedford, Mass.). The relative intensity of gamma-gamma bands were scanned and compared for FXIIIa inhibition, while alpha bands were scanned and compared for tTG inhibition. No cross-linking was detected in the negative controls containing only FXIII-free fibrinogen thrombin and DMSO. Complete cross-linking was seen in positive controls containing fibrinogen, enzyme (FXIIIa or tTG), calcium, and thrombin in the absence of inhibitor. The inhibition results obtained from PAGE of samples prepared as described above, and containing ZG-1400a at 100 μM and 10 μM, or cerulenin or iodoacetamide at 1 mM, 100 μM, and 10 μM, are shown in Table 2.

TABLE 2

Inhibition of FXIIIa and tTG based on densitometer readings.

| Compound | Concentration | % FXIIIa Inhibition[1] | % tTG Inhibition[2] |
|---|---|---|---|
| ZG-1400 | 100 μM | 100 | 83 |
|  | 10 μM | 66 | 80 |
| Iodoacetamide | 1 mM | 100 | 60 |
|  | 100 μM | 100 | 68 |
|  | 10 μM | 66 | 72 |
| Cerulenin | 1 mM | 100 | 94 |
|  | 100 μM | 38 | 79 |
|  | 10 μM | 8 | 30 |

[1]Gamma-gamma bands scanned
[2]Alpha bands scanned

FVIIa Inhibition Assay

For the FVIIa, FXa and thrombin inhibition assays described below, an inhibition assay buffer containing 50 mM Tris, 5 mM CaCl$_2$, 150 mM NaCl, 0.1% Tween 20, and 0.1% BSA (albumin, bovine, Sigma fraction V (Sigma)) at about pH 8.0 was used 2. For each of the inhibition assays, the total reaction volume was 100 μl and the assays were performed in 96-well plates.

For the FVIIa inhibition assay, about 30 μl of inhibition assay buffer, 25 μl of 20 nM recombinant FVIIa (Walt Kiesel, University of New Mexico), and 10 μl of one of a series of dilutions of ZG-1400a were added to plate wells. The ZG-1400a was prepared in 10% DMSO and tested using half-log dilutions, starting at a final assay concentration of 100 μM and diluting to 1 nM. A negative (no inhibition) control contained 30 μl inhibition assay buffer, 25 μl of 20 nM FVIIa, and enough DMSO to give a 1% final DMSO concentration.

The test and control wells were incubated for about 10 min at room temperature. After incubation, 25 μl of 20 nM tissue factor (Walt Kiesel, University of New Mexico) was added to the wells and incubated for a second 10 min period at room temperature. After the second incubation period, 10 μl of 10 mM H-D-isoleucyl-L-arginine-p-nitroanilide-dihydrochloride (S2288 substrate, Kabi, Stockholm, Sweden) was added to each well.

In this assay, not even the highest concentration of ZG-1400a assayed (100 μM) inhibited FVIIa activity. This determination was made by reading absorbance at 405 nm on a ThermoMax microplate reader.

Factor IX Inhibition Assay

60 μl buffer, 10 μl of 40 nM FIX, and 10 μl of one of a series of dilutions of ZG-1400a were added to plate wells. The buffer contained 150 mM NaCl, 5 mM CaCl$_2$, 25 mM Tris, pH 8.0, and 0.1% polyethyleneglycol (PEG). The ZG-1400a was prepared in 10% DMSO and tested using half-log dilutions, starting at a final assay concentration of 100 μM and diluting to 1 nM. A negative (no inhibition) control contained 60 μl buffer, 10 μl of 40 nM FIX, and enough DMSO to give a 1% final DMSO concentration.

The test and control wells were incubated approximately 10 min at room temperature. After incubation, approximately 10 μl of a mixture containing 200 nM FX (Walt Kiesel, University of New Mexico), 500 pM FVIII (Novo Nordisk) and 10 μM PCPS (phosphatidylcholine:phosphatidylserine (Sigma) in a 1:1 ratio) was added to each well. Then 10 μl of 1 mM S2765 substrate (Kabi) was added to each well.

In this assay, FIX converts FX to FXa. Not even the highest concentration of ZG-1400a assayed (100 μM) inhibited FIX activity. This determination was made by reading absorbance at 405 nM on a ThermoMax microplate reader.

Factor Xa Inhibition Assay

About 30 μl inhibition assay buffer, 50 μl of 10 nM FXa and 10 μl of one of a series of dilutions of ZG-1400a were added to plate wells. The ZG-1400a was prepared in 10% DMSO and tested using half-log dilutions, starting at a final assay concentration of 100 μM and diluting to 1 nM. A negative (no inhibition) control contained 30 μl inhibition assay buffer, 50 μl of 10 nM FXa, and enough DMSO to give a 1% final DMSO concentration.

The test and control wells were incubated for about 10 min at room temperature. After the incubation period, 10 mM N-α-benzyloxycarbonyl-D-arginine-L-glycyl-L-arginyl-p-nitroanilide-dihydrochloride (S2765 substrate, Kabi) was added to each well.

In this assay, not even the highest concentration of ZG-1400a assayed (100 μM) inhibited FXa activity. This determination was made by reading absorbance at 405 nM on a ThermoMax microplate reader.

Thrombin Inhibition Assay

About 30 μl inhibition assay buffer, 50 μl of 2 μg/ml thrombin (bovine, Enzyme Research Labs), and 10 μl of one of a series of dilutions of ZG-1400a were added to plate wells. The ZG-1400a was prepared in 10% DMSO and tested using half-log dilutions, starting at a final assay concentration of 100 µM and diluting to 1 nM. A negative (no inhibition) control contained 30 µl inhibition assay buffer, 50 µl of 2 µg/ml thrombin, and enough DMSO to give a 1% final DMSO concentration.

The test and control wells were incubated for about 10 min at room temperature. After the incubation period, 20 µl of 1 mM SPECTROZYME TH (H-D-hexahydrotyrosyl-L-alanyl-L-arginine-p-nitroanilide-diacetate salt, American Diagnostica, Inc., New York, N.Y.) was added to each well.

In this assay, not even the highest concentration of ZG-1400a assayed (100 µM) inhibited thrombin activity. This determination was made by reading absorbance at 405 nM on a ThermoMax microplate reader.

Plasma clot Lysis Assay

For this assay, 50 µl of one of a series of concentrations of iodoacetic acid, cerulenin, or ZG-1400a was added to 0.5 ml human citrated plasma (prepared from one blood donor) in 5 ml polypropylene tubes. The ZG-1400a and iodoacetic acid were individually prepared in 10% DMSO and tested using half-log dilutions, starting at a final assay concentration of 100 µM and diluting to 10 µM. Cerulenin was prepared in 10% ethanol and tested using half-log dilutions, starting at a final assay concentration of 100 µM and diluting to 10 µM. A negative (no inhibition) control for ZG-1400a and iodoacetic acid was 50 µl of 10% DMSO to give a final assay concentration of 1% DMSO in each control tube. A negative control for cerulenin was 50 µl of 10% ethanol to give a final assay concentration of 1% ethanol in each control tube.

Approximately $10^6$ cpm $^{125}$I-fibrinogen (Amersham), 50 mM $CaCl_2$ (20 mM above citrate concentration) and 5 units thrombin (bovine, Enzyme Research Labs) were added to each test and control tube. The tubes were incubated while rocking for 20 h at 37° C. Plasma clots formed in the tubes were washed three times with about 1 ml phosphate buffered saline (PBS). The plasma clots in each tube were counted after the PBS washes.

Approximately 2 ml of 50 mM Tris, pH 7.4, containing 50 mM NaCl, 28 µg plasminogen (human, Calbiochem), and 280 ng urokinase (human, Calbiochem) were added to the clots in test and control tubes. At 1, 2, and 4 h intervals, 25 µl aliquots of the samples were removed from each tube and counted.

Only plasma clots formed in the presence of 100 µM iodoacetic acid, cerulenin or ZG-1400a were significantly more susceptible to lysis by plasminogen and urokinase. The values shown in Table 3 represent the amount of lysis after plasma clots were formed for about 20 h and exposed to plasminogen and urokinase for about 4 h.

TABLE 3

Percent lysis of plasma clots

| Compound[1] | % Plasma Clot lysis |
|---|---|
| ZG-1400 | 46 |
| Iodoacetic Acid | 23 |
| Cerulenin | 97 |

[1]100 µM per compound

Papain Inhibition Assay

For the papain inhibition assay, a buffer containing 0.1M $NaPO_4$ and 2.5 mM EDTA at about pH 7.0 was used. An Azocoll™ solution was prepared by adding 5 mg Azocoll™ (Calbiochem; an insoluble, powdered cowhide to which a bright red dye is attached (azo-dye-bound collagen)) to the buffer while stirring. The Azocoll was prewarmed to about 37° C. 10 µl of 0.1M L-cysteine, 10 µl of 50 µg/ml papain (Boehringer Mannheim), 0.5 ml of Azocoll solution, and 50 µl of one of a series of concentrations of ZG-1400a, iodoacetamide, iodoacetic acid, cerulenin, or 50 µl of the DMSO or ethanol negative controls were added to duplicate 13×75 mm glass tubes. The ZG-1400a, iodoacetamide, and iodoacetic acid were individually prepared in 10% DMSO and tested using half-log dilutions, starting at a final assay concentration of 100 µM and diluting to 10 nM. Cerulenin was prepared in 10% ethanol and tested using half-log dilutions, starting at a final assay concentration of 100 µM and diluting to 10 nM. A negative (no inhibition) control for ZG-1400a, iodoacetamide and iodoacetic acid was 50 µl of 10% DMSO to give a final assay concentration of 1% DMSO in each control tube. A negative control for cerulenin was 50 µl of 10% ethanol to give a final assay concentration of 1% ethanol in each control tube. The test and control tubes then were incubated for 30 min at 37° C. in an agitated water bath.

After incubation, all of the tubes were centrifuged at 2000 RPM for 5 min. The supernatant was removed and its absorbance was read at 520 nm on a Beckman DU640 spectrophotometer to determine the amount of papain inhibition.

ZG-1400a and cerulenin did not inhibit papain activity, while iodoacetamide and iodoacetic acid did cause inhibition. Table 4 shows the comparative papain $IC_{50}$ results for ZG-1400a, iodoacetamide, iodoacetic acid and cerulenin.

TABLE 4

Inhibitory Concentration ($IC_{50}$) Values - Papain inhibition Assay

| Compound | Papain Inhibition |
|---|---|
| ZG-1440 | No inhibition |
| Iodoacetamide | 10 nM |
| Iodoacetic Acid | 700 nM |
| Cerulenin | No inhibition |

Administration Of ZG-1400a

Two agents that are often used to prevent clot formation are tissue plasminogen activator and streptokinase. These agents activate normal plasmin, but have no effect on resolution of clots that have formed (e.g., no effect on clot cross-linking and stabilization).

The FXIII inhibitors of the present invention are contemplated to be advantageous for use in therapeutic applications in which clot resolution is desired. More specifically, these compounds are useful when inhibition of FXIIIa-mediated cross-linking of fibrin in clots in a recipient is needed. Such applications for FXIIIa inhibitors of the present invention include diseases, disorders, and surgical interventions where enhanced fibrinolysis of new and/or old clots is useful. More specifically, the FXIIIa inhibitors of the invention may be advantageously administered to patients that have suffered a myocardial infarction, or that have recently undergone angioplasty or other cardiovascular procedures that can lead to arterial stenosis or restenosis. In addition, these FXIIIa inhibitors may be used as general profibrolytic agents, and may be beneficially administered to recipients suffering from stroke, phlebitis, deep vein thrombosis, disseminated intravascular coagulation, arterial occlusion or pulmonary embolism. The claimed FXIIIa inhibitors also may be advantageously used in combination with plasminogen, with one or more plasminogen activators, or with a combination of plasminogen and one or more plasminogen activators.

FXIIIa inhibitors of the present invention can be formulated with a pharmaceutically acceptable carrier for parenteral, oral, nasal, rectal, or transdermal administration or the like, according to conventional methods. Formulations may further include one or more diluents, fillers, emulsifiers, preservatives, buffers, excipients, and the like, and may be provided in such forms as liquids, powders, emulsions, suppositories, liposomes, transdermal patches and tablets, for example. Because of their ease of administration, tablets and capsules represent the most advantageous oral dosage unit form. Accordingly, suitable carriers for tablets and capsules include starches, sugars, diluents, granulating agents, lubricants, binders, disintegrating agents and the like. One skilled in the art may formulate the compounds of the present invention in an appropriate manner, and in accordance with accepted practices, such as those disclosed in *Remington's Pharmaceutical Sciences*, Gennaro (ed.), Mack Publishing Co., Easton, Pa. 1990 (which is incorporated herein by reference in its entirety). The claimed compounds may also be administered in the form of liposomes or sustained release formulations, or by means of implantable pumps or implantable slow release devices, to achieve a consistent dosage over an extended period of time.

Exemplary therapeutic dosage levels of FXIIIa inhibitors are those that produce an acceleration of clot fibrinolysis. The exact dose for an individual patient will be determined by the clinician according to accepted standards, taking into account the nature and severity of the condition to be treated, age, weight, and general health of the patient, and other factors evident to those skilled in the art. Determination of dose is within the level of ordinary skill in the art. For instance, data from accepted animal models are generally predictive of doses in humans to within one order of magnitude. The dog coronary artery thrombosis model is an exemplary animal model in this regard. Therapeutic doses in humans can range from about 1 µg to about 100 mg FXIIIa inhibitor per kg body weight of recipient per day. In some instances, after initial resolution of one or more formed clots, a lower dosage level may be administered to maintain the desired fibrinolytic effect.

The oral absorption of FXIIIa inhibitors can be further enhanced by use of drug permeation enhancers, such as salicylates; surfactants such as bile acids and their salts, polyoxyethylene fatty acids or fatty acyl ethers; chelating agents such as ethylenediamine tetraacetic acid; and solvents such as dimethylsulphoxide and ethanol (Verhoef et al., *Eur. J. Drug Metb. Pharmacokinet.* 15:83–93, 1990).

Pharmaceutical compositions of the present invention are administered in unit dosage form at daily to weekly intervals, in single or multiple doses, or by continuous infusion. An "effective amount" of such a pharmaceutical composition is an amount that provides clinically significant clot resolution and/or fibrinolysis.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A pharmaceutical composition comprising a compound having the structure:

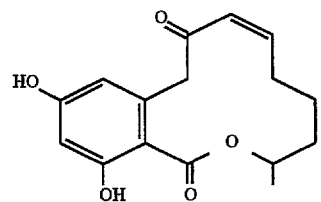

a buffer, and a pharmaceutically acceptable vehicle.

2. A pharmaceutical composition comprising a compound having the structure:

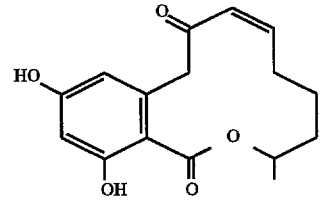

a pharmaceutically acceptable vehicle, and a fibrinolytic agent.

3. The pharmaceutical composition of claim 2, wherein the fibrinoloytic agent is selected from the group consisting of plasminogen, one or more plasminogen activators; and a combination of plasminogen and one or more plasminogen activators.

4. A method for inhibiting FXIIIa catalysis of fibrin cross-linking in vivo comprising:

administering to a recipient a therapeutic amount of a pharmaceutical composition comprising a compound having the structure:

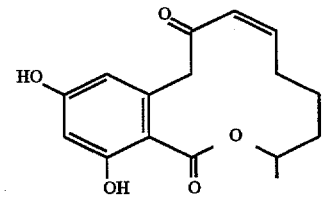

and a pharmaceutically acceptable vehicle, in an amount sufficient to inhibit FXIIIa catalysis of fibrin cross-linking.

5. The method of claim 4 further comprising the step of administering to the recipient a fibrinolytic agent selected from the group consisting of plasminogen; one or more plasminogen activators; and a combination of plasminogen and one or more plasminogen activators.

6. The method of claim 5, wherein the fibrinolytic agent is administered before, after or concurrent with administration of the pharmaceutical composition.

7. The method of claim 5, wherein the recipient is at high risk of thrombosis.

8. The method of claim 7, wherein the recipient has a medical indication selected from the group consisting of: myocardial infarction; an occluded artery; stroke; phlebitis; deep vein thrombosis; disseminated intravascular coagulation; and pulmonary embolism.

9. The method of claim 7, wherein the recipient has undergone or will undergo a medical procedure that disposes the recipient to blood clot formation.

* * * * *